(12) United States Patent
Blount et al.

(10) Patent No.: US 8,775,344 B2
(45) Date of Patent: Jul. 8, 2014

(54) DETERMINING AND VALIDATING PROVENANCE DATA IN DATA STREAM PROCESSING SYSTEM

(75) Inventors: Marion Lee Blount, Mahopac, NY (US); John Sidney Davis, II, Arlington, VA (US); Maria Rene Ebling, White Plains, NY (US); Archan Misra, Bridgewater, NJ (US); Daby Mousse Sow, Croton on Hudson, NY (US); Min Wang, Cortlandt Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 1284 days.

(21) Appl. No.: 12/125,219

(22) Filed: May 22, 2008

(65) Prior Publication Data

US 2009/0292818 A1    Nov. 26, 2009

(51) Int. Cl.
*G06F 17/00* (2006.01)
*G06N 3/00* (2006.01)

(52) U.S. Cl.
USPC .............................. 706/45; 713/176; 709/230

(58) Field of Classification Search
USPC ......................................................... 706/45
See application file for complete search history.

(56) References Cited

U.S. PATENT DOCUMENTS

| | | | |
|---|---|---|---|
| 6,131,091 A | 10/2000 | Light | |
| 6,594,773 B1 | 7/2003 | Lisitsa et al. | |
| 6,658,477 B1 | 12/2003 | Lisitsa et al. | |
| 6,725,287 B1 | 4/2004 | Loeb et al. | |
| 6,748,440 B1 | 6/2004 | Lisitsa et al. | |
| 6,983,286 B1 | 1/2006 | Sinha et al. | |
| 7,010,538 B1 | 3/2006 | Black | |
| 7,194,000 B2 | 3/2007 | Balachandran et al. | |
| 7,222,182 B2 | 5/2007 | Lisitsa et al. | |

(Continued)

FOREIGN PATENT DOCUMENTS

EP      852440 A2  *  7/1998

OTHER PUBLICATIONS

M. Blount et al., "A Time-and-Value Centric Provenance Model and Architecture for Medical Event Streams," International Conference on Mobile Systems, Application and Services, Proceedings of the 1st ACM SIGMOBILE International Workshop on Systems and Networking Support for Healthcare and Assisted Living Environments, Jun. 11, 2007, pp. 95-100.

(Continued)

*Primary Examiner* — Alan Chen
*Assistant Examiner* — Kalpana Bharadwaj
(74) *Attorney, Agent, or Firm* — Preston J. Young; Ryan, Mason & Lewis, LLP

(57) ABSTRACT

Techniques are disclosed for determining and validating provenance data in such data stream processing systems. For example, a method for processing data associated with a data stream received by a data stream processing system, wherein the system comprises a plurality of processing elements, comprises the following steps. Input data elements and output data elements associated with at least one processing element of the plurality of processing elements are obtained. One or more intervals are computed for the processing element using data representing observations of associations between inputs elements and output elements of the processing element, wherein, for a given one of the intervals, one or more particular input elements contained within the given interval are determined to have contributed to a particular output element. In another method, intervals are specified, and then validated by comparing the specified intervals against intervals computed based on observations.

20 Claims, 7 Drawing Sheets

(56) References Cited

U.S. PATENT DOCUMENTS

| | | | |
|---|---|---|---|
| 7,240,065 | B2 | 7/2007 | Yang et al. |
| 7,246,157 | B2 | 7/2007 | Cianciarulo et al. |
| 7,251,660 | B2 | 7/2007 | Yang et al. |
| 7,680,797 | B1 | 3/2010 | Singh et al. |
| 2003/0076784 | A1 | 4/2003 | Ta et al. |
| 2003/0084179 | A1 | 5/2003 | Kime et al. |
| 2003/0126276 | A1 | 7/2003 | Kime et al. |
| 2004/0117037 | A1 | 6/2004 | Hinshaw et al. |
| 2005/0010510 | A1* | 1/2005 | Brose et al. ............ 705/35 |
| 2005/0185578 | A1 | 8/2005 | Padmanabhan et al. |
| 2006/0004802 | A1 | 1/2006 | Phillips et al. |
| 2006/0126713 | A1 | 6/2006 | Chou et al. |
| 2006/0149849 | A1 | 7/2006 | Raz |
| 2006/0197766 | A1 | 9/2006 | Raz |
| 2006/0288045 | A1 | 12/2006 | Raz |
| 2007/0043565 | A1 | 2/2007 | Aggarwal et al. |
| 2007/0088957 | A1* | 4/2007 | Carson ............ 713/176 |
| 2008/0201381 | A1* | 8/2008 | Desai et al. ............ 707/200 |

OTHER PUBLICATIONS

C. E. Shannon, "A Mathematical Theory of Communication," Bell System Technical Journal, Jul. and Oct. 1948, pp. 1-55, vol. 27.

L. Moreau et al., "The Provenance of Electronic Data," Communications of the ACM, Apr. 2008, pp. 52-58, vol. 51, No. 4.

N.N. Vijayakumar et al., "Tracking Stream Provenance in Complex Event Processing Systems for Workflow-Driven Computing," Second International Workshop on Event-driven Architecture, Processing, and Systems (EDA-PS'07), in conjunction with VLDB'07, Sep. 2007, 8 pages, Vienna, Austria.

R. Lempel et al., "Predictive Caching and Prefetching of Query Results in Search Engines," WWW '03 Proceedings of the 12th International Conference on World Wide Web, pp. 19-28, May 2003, Budapest, Hungary.

* cited by examiner

FIG. 2

| INPUT STREAM | OUTPUT STREAM |
|---|---|
| $X_{-M+1}\ X_{-M+2}\ \ldots\ X_{-5}\ X_{-4}\ X_{-3}\ X_{-2}\ X_{-1}\ X_0$ | $Y_0$ |
| $X_{-M+2}\ X_{-M+3}\ \ldots\ X_{-4}\ X_{-3}\ X_{-2}\ X_{-1}\ X_0\ X_1$ | $Y_1$ |
| $X_{-M+3}\ X_{-M+4}\ \ldots\ X_{-3}\ X_{-2}\ X_{-1}\ X_0\ X_1\ X_2$ | $Y_2$ |
| $X_{-M+4}\ X_{-M+5}\ \ldots\ X_{-2}\ X_{-1}\ X_0\ X_1\ X_2\ X_3$ | $Y_3$ |
| ... | ... |

DETERMINING AND VALIDATING PROVENANCE DATA IN DATA STREAM PROCESSING SYSTEM

CROSS REFERENCE TO RELATED APPLICATION

The present application is related to U.S. patent application identified as U.S. Ser. No. 12/125,212, entitled "Method and Apparatus for Maintaining and Processing Provenance Data in Data Stream Processing System," and filed concurrently herewith, the disclosure of which is incorporated herein.

FIELD OF THE INVENTION

The present invention relates to data stream processing systems and, more particularly, to techniques for determining and validating provenance data in such data stream processing systems.

BACKGROUND OF THE INVENTION

Many data sources around us produce high volume streams containing significant amounts of important information for specific applications. Example applications are video surveillance applications ingesting many video feeds to detect potential security breaches. Another example is continuous health monitoring where patients are surrounded with sensors emitting stream data into a stream processing infrastructure that analyzes the data to identify and report medically significant events to medical professionals.

In most of these applications, it is important to track the provenance of every event generated by the system. By provenance, it is meant the origins and justification for the generation of events by the system. For instance, if a medical system suggests that a patient requires a drug dosage change, based on its analysis, the provenance of such an event would inform the medical professionals of the procedure and all the data points used for the generation of that alert.

Typically, these provenance reports are manually obtained by leveraging data specified by developers during the design of their analysis.

SUMMARY OF THE INVENTION

Principles of the invention provide techniques for determining and validating provenance data in such data stream processing systems For example, in one embodiment of the invention, a method for processing data associated with a data stream received by a data stream processing system, wherein the system comprises a plurality of processing elements, comprises the following steps. Input data elements and output data elements associated with at least one processing element of the plurality of processing elements are obtained. One or more intervals are computed for the processing element using data representing observations of associations between input elements and output elements of the processing element, wherein, for a given one of the intervals, one or more particular input elements contained within the given interval are determined to have contributed to a particular output element.

In another embodiment, a method for processing data associated with a data stream received by a data stream processing system, wherein the system comprises a plurality of processing elements, comprises the following steps. Input data elements and output data elements associated with at least one processing element of the plurality of processing elements are obtained. One or more intervals are specified for the processing element wherein, for a given one of the intervals, one or more particular input elements contained within the given interval are believed to have contributed to a particular output element. The one or more specified intervals are validated by computing one or more intervals for the processing element using data representing observations of associations between input elements and output elements of the processing element, and comparing the one or more specified intervals and the one or more computed intervals.

Advantageously, such inventive techniques are able to determine dependencies between input data elements and output data elements for one or more processing elements in the data stream processing system. That is, dependency equations may be determined allowing the system to identify which input stream elements were used in the generation of a given output stream element.

These and other objects, features and advantages of the present invention will become apparent from the following detailed description of illustrative embodiments thereof, which is to be read in connection with the accompanying drawings.

BRIEF DESCRIPTION OF THE DRAWINGS

FIG. 2 illustrates a data format, according to an embodiment of the invention.

DETAILED DESCRIPTION

Figure 1:
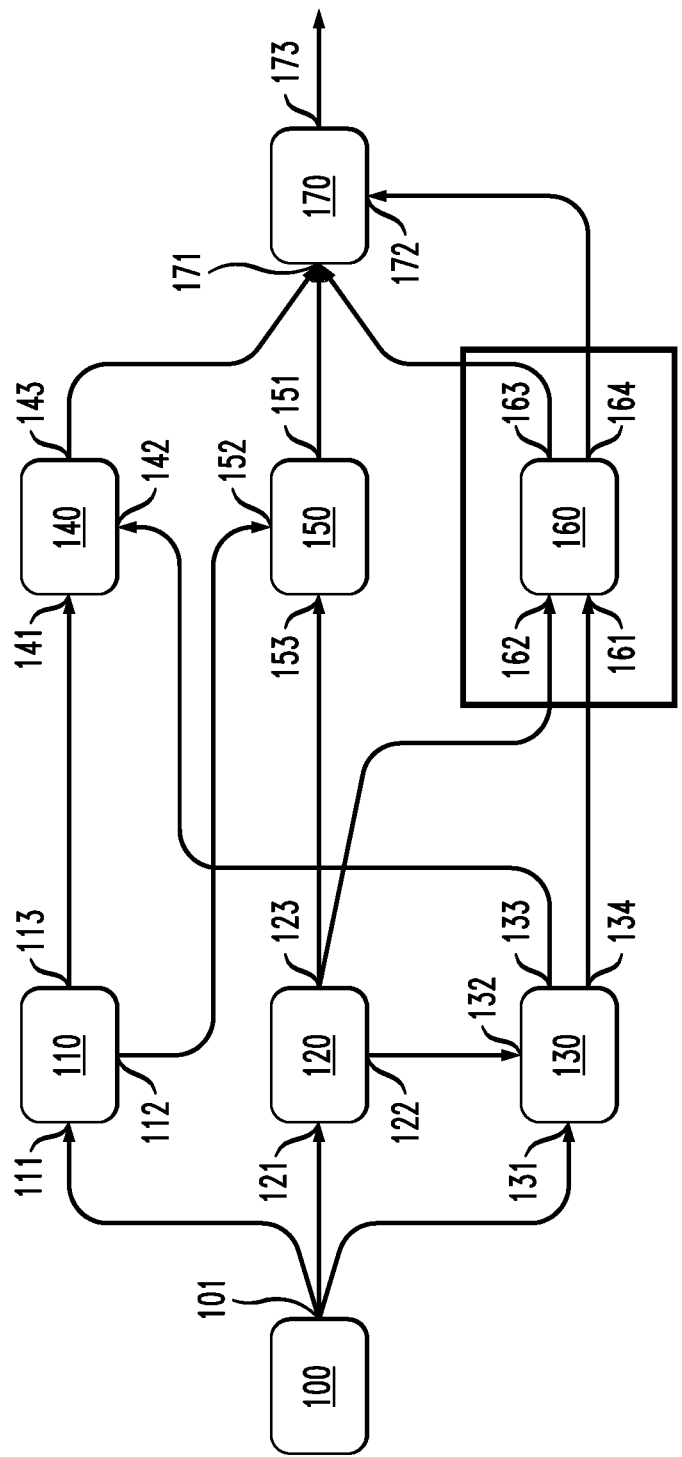
FIG. 1 illustrates a graph of analysis components, according to an embodiment of the invention.

Embodiments of the present invention will be explained below in the context of an illustrative data stream processing system. However, it is to be understood that the present invention is not limited to any particular data processing system. Rather, the invention is more generally applicable to any data processing system in which it would be desirable to determine and validate provenance data. As illustratively used herein, the term "provenance" is defined as "origin" or "source." Thus, for example, provenance data (or provenance information) is meta-information that documents the origin or source data, generally where that data was derived from other data through, for example, complex, multi-layered analysis. Also, the term "empirical" as used herein is defined as "provable or verifiable by experience or experiment." We characterize computations to be "offline" when they are given the entire inputs in advance [for example, see http://www.nist.gov/dads/HTML/offline.html]. In contrast, on-line computations gradually incorporate newly received inputs in the computations.

The illustrative real-world, practical application of principles of the invention is the domain of healthcare. Specifically, in the healthcare domain, one might envision a stream processing infrastructure that takes, as input, streams of medical information such as streams of electroencephalogram (EEG) or electrocardiogram (ECG) data as well as blood pressure, weight, or even glucometer readings. The stream processing infrastructure would apply analytic algorithms to these data streams and identify significant medical events that warrant further attention from a doctor or other medical professional. In such a system, it is important to give the medical professional as much information about the generation of the significant medical event as possible, including meta-information, referred to herein as provenance data, such as what subsets of the streams triggered the significant medical event and what specific processing elements contributed to its generation. The medical professional who receives the alert generated by the stream processing system may issue a provenance query related to the alert, where the provenance query is a request to show or reveal the stream data items and the stream processing nodes that contributed to the generation of the alert. Again, it is to be appreciated that while the solution domain mentioned in this embodiment is healthcare, principles of the invention apply to any domain where processing of data streams can be applied.

In particular, as will be explained, illustrative principles of the invention provide automated generation of dependency equations in a stream provenance system. In addition, we present techniques to validate dependency equations specified by developers, against derived dependency equations generated automatically by our system. In an illustrative embodiment, we propose a Provenance Dependency Deriver (PDD) component that is added to the stream processing system and that observes, for any given stream processing component, the sequence of input data elements (belonging to one or more distinct streams) and the corresponding sequence of output data elements. The job of the PDD is to treat the processing component as a black box and simply learn, on the basis of the observed data, the time-windows of input data that seem to empirically affect the generation of a corresponding output data element. Hence, a main goal of the PDD component is to establish a time-invariant temporal dependency function. In general, the PDD component establishes a relationship of the form:

$$e_i(t) \Leftarrow \bigcup_{j:S_j \text{ is input to } PE_i} \bigcup_{k=1}^{L_j} \{e : e \in S_j(^{t-}start_{jk}, ^{t-}end_{jk})\} \quad (1)$$

Here, $L_j$ is the number of distinct disjoint 'time intervals' which define the values of $S_j$ on which $e_i(t)$ depends, and $start_{jk}$ and $end_{jk}$ define the boundaries of these intervals. The term 'time-invariant' refers to the fact that the terms $start_{jk}$ and $end_{jk}$ are themselves independent of t; as a consequence, the dependence of a derived event to other input data elements can be expressed succinctly and completely independently of the specific timestamp or ID (identifier) of each sample. A main goal here is to try to infer the values of the terms $start_{jk}$ and $end_{jk}$. In many practical cases, the temporal dependency model can be simplified to the specification of a single (per-stream) interval term $\Delta_j$ (for each input stream $S_j$), such that the dependency is purely on the most recent window of input events:

$$e_i(t) \Leftarrow \bigcup_{S_j \text{ is input to}} PE_i\{e \in S_j(t, t - \Delta_j)\} \quad (2)$$

Here, $\Delta_j$ represents the past "time-window" associated with input stream $S_j$.

By way of example, we can use one of several different sets of techniques to ascertain the values of these terms. A first illustrative approach is applicable to processing components that are known to perform 'linear' (i.e., affine) transformations of the input data using principal component analysis or the Karhunen-Loeve transform [see Digital Pictures Representation, Compression and Standards (Applications of Communications Theory), Arun N. Netravali, Barry G. Haskell, Plenum Press, 1995, the disclosure of which is incorporated herein]. Another illustrative approach is to model our components with linear systems and perform impulse response or frequency response tests to estimate a transfer function. From this transfer function, the input-output dependencies can be obtained.

Another illustrative approach, and the one described further below, uses information theoretic constructs to measure input output correlations and infer input output dependencies. This approach makes no assumptions on the components and applies to the general class of linear and non-linear transformations. It involves the use of empirical joint probability distribution functions and the computation of information-theoretic concepts, such as entropy and mutual information. For example, we can start by computing a sequence of conditional entropies between the output Y and increasingly longer input sequences X(.). In other words, we compute H(Y(t)); H(Y(t)|X(t)), H(Y(t)|X(t), X(t−1), H(Y(t)|X(t), X(t−1), X(t−2)) . . . and so on, where H(Y(t)) refers to the Shannon entropy [see C. E. Shannon, "A mathematical theory of communication," Bell System Technical Journal, vol. 27, pp. 379-423 and 623-656, July and October, 1948, the disclosure of which is incorporated herein] of the random variable Y(t). In general, as long as there is some dependence, the additional conditioning will result in the reduction of the conditional entropy. Thus, we can keep computing the conditional entropies (based on the empirical distributions), until we reach a value L such that H(Y|X,X−1, X−(L+1)) results in no or insignificant reduction in entropy compared to H(Y|X, X(t−1), X(t−L)) or the entropy itself drops below an acceptable maximal value. We can then declare L to be the appropriate time interval for which dependence has been observed.

In addition to this basic description, there are many other details, illustrating many different variants of this invention. One key aspect of the invention is the use of the PDD based dependency functions to perform validation of externally specified dependencies. In particular, the system may compare the empirically derived dependency values with the values externally (e.g., manually) specified for a stream processing component and note the extent of divergence. If the degree of divergence is high, this may be an indicator of either an incorrectly specified dependency function or some faulty operation of the actual processing logic in the stream processing component. In many situations, such automatic identification of potential faults or anomalies can prove invaluable as a tool for validation or early fault detection.

While the basic description above refers to inferring the temporal dependency from the observed input and output values, principles of the invention also accommodate situations where the processing component can be fed (in a simulated or test environment) with specific input samples generated by the PDD itself. In this case, the derived dependency function can often be more accurate, as the sequence or set of input elements can often be chosen more intelligently to represent a wider sample space. For example, in medical stream analysis environments, it is possible that certain input values occur only rarely or under significant anomalies (e.g., heart rate readings below 40); as such, during normal operation, the stream processing system would be likely not to observe such input conditions. However, using simulated values allows the PDD to observe the input-output dependency over a much wider range of operating parameters.

While the invention has so far described only a basic temporal model of dependency, the techniques of the invention can also be applied to learn or infer some alternate models of dependency, assuming of course, that the 'model' of dependency is externally provided. For example, if the dependency is declared to be in terms of the 'number of past elements' and not in terms of time windows, then the inventive approach can be applied here as well. We simply have to form an empirical matrix as described in FIG. 2, using appropriate sequences of input elements X in the appropriate columns, and then apply the techniques as before to determine the 'sequence interval' L (instead of a time interval).

The method described above can either be applied offline (to a set of stored input and output streams) or online. In the offline case, principles of the invention provide for the PDD to access a set of stored input and output streams (over an appropriately defined history) and use this set as a 'learning sequence' to derive the dependencies. In the online model, the PDD can continually observe the incoming input elements and the generated output elements, and then incrementally construct a larger empirical matrix, and thus continually derive more-refined estimates of the dependency values as the empirical matrix evolves.

The method described so far is blind—it tries to ascertain the empirical dependencies using all samples of input and output elements, potentially increasing the time window until the dependency function (e.g., the conditional entropy) is observed to remain steady (below a specified threshold) or the resulting entropy is small enough. However, principles of the invention can also be combined with additional prior specifications that refine the selected set of input elements that are used in the empirical derivation process. For example, the processing component may have some external specifications (e.g., indicating that it only utilizes heart rate readings taken on Monday mornings or blood pressure readings taken while in the gym); the PDD can apply such externally-specified filters to first reduce the vector space of input data elements that may be potentially associated with an output element. The subsequent technique of determining the appropriate minimal set of input elements remains the same.

The method described can also be applied to construct equivalence classes of temporal or sequence-based provenance dependence—conceptually, an equivalence class may be defined to a set of output values (a subset of the range of output values) such that all members of this set have an identical or similar dependence function over their corresponding input elements. Such a situation arises, for example, if the output from a processing component is dependent on the past 100 values if the output value is greater than 40, but dependent on the past 1000 samples if the output is less than 40. Such segmentation of the window of dependency can be done either blindly (without any prior segmentation of the output range) or with the help of prior specifications on the output segments (in which case, principles of the invention can still be used to determine if multiple segments can be combined into one equivalence class).

Such segmentation helps to further refine the provenance dependency—instead of defining a broad window of dependence for all output values, the method described above can potentially associate a more restricted and accurate window of dependence for certain ranges of output values. Moreover, forming as many elements as possible into one equivalence class also reduces the storage space needed to store the derived provenance dependency functions. In particular, a simple embodiment of this approach would be to first partition the output space into an appropriate set of partitions, and assign the empirically observed output elements into their corresponding partitions. The statistical analysis techniques described above can then be applied on each partition of data independently to derive its temporal or sequence-based dependence. If the derived dependence for multiple partitions turns out to be identical (or within a specified tolerance, such as the length of the time window $\Delta$ being within +/−2 of each other), then the partitions may be replaced by one equivalent partition, with one corresponding combined dependency function.

Exemplary systems and methods for supporting multi-user collaborative software development environments will now be discussed in greater detail with reference to the exemplary figures in which the same reference numbers denote the same or similar elements. It is to be understood that the systems and methods described herein in accordance with the present invention may be implemented in various forms of hardware, software, firmware, special purpose processors, or a combination thereof. In particular, in one exemplary embodiment, systems and methods of the invention are implemented in software comprising program instructions that are tangibly embodied on one or more program storage devices (e.g., hard disk, magnetic floppy disk, RAM, CD ROM, DVD, ROM and flash memory), and executable by any device or machine comprising suitable architecture.

It is to be further understood that because the constituent system modules and method steps depicted in the accompanying figures can be implemented in software, the actual connections between the system components (or the flow of the process steps) may differ depending upon the manner in which the application is programmed. Given the teachings herein, one of ordinary skill in the related art will be able to contemplate these and similar implementations or configurations of the present invention.

FIG. 1 shows a graph of analysis components. This graph has eight processing elements (PE): 100, 110, 120, 130, 140, 150, 160, and 170. The processing elements are connected via communication paths represented by the directional arrows connecting them. As each processing element processes the stream according to its individual algorithm, which could perform any computation on the stream of data, the processing element passes the resultant output to the next processing element according to the connections in the graph. We can illustratively describe the subject of the invention as the problem of learning, at each processing element, dependency equations that allow the system to identify which input stream elements were used in the generation of a given output stream element. As shown in FIG. 1, data streams arriving on the ports 111, 121, 131, 132, 141, 142, 152, 153, 161, 162, 171, and 172 are input to respective processing elements and elements are output by the respective processing elements on the corresponding output ports 101, 112, 113, 122, 123, 133, 134, 143, 151, 163, 164, and 173. In FIG. 1 it may be observed that the data elements arriving at ports 111, 121 and 132 are identical, corresponding to the data elements generated by the output port 101.

Figure 6:
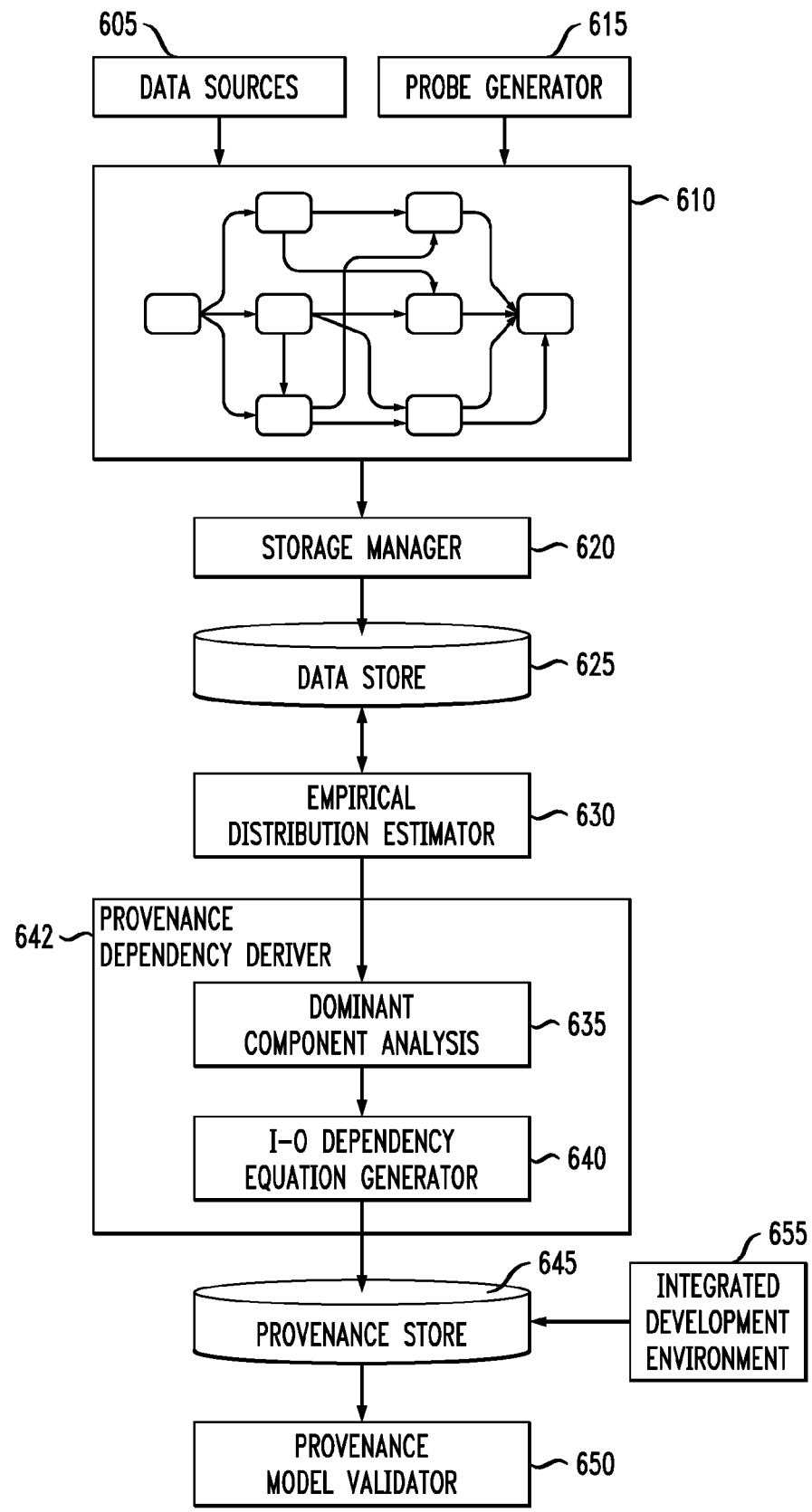
FIG. 6 illustrates a provenance system, according to an embodiment of the invention.

FIG. 6 depicts an illustrative architecture for the system. Data sources 605 generate events and provide these events for display in an analysis graph 610 of processing elements. Alternately, the events may be generated by the Probe Generator 615, which is specifically generating input events that help in the more accurate or more exhaustive derivation of the dependency windows. The persistency of all streams of events flowing in the graph is performed by a storage manager 620 into a data store 625. To statistically infer input-output dependency equations, empirical probability distributions are estimated. The empirical distribution estimator 630 accesses the data store 620 to estimate these distributions. These distributions are used by the dominant component analysis module 635 to identify the position in the input streams of the component that is mainly responsible for the generation of the output. It is inside the dominant component analysis module 635 that conditional entropies and mutual information estimates are computed from empirical probability distributions to identify dominant components in the input. These dominant components are the parts of the input that are mostly responsible for the value of the output for a given processing element.

Once such components are identified, the I-O (input-output) Dependency Equation Generator 640 generates I-O dependency equations and stores them in the provenance store 645. The Provenance Dependency Deriver 642 is in essence composed of the Dominant Component Analysis module 635 and the I-O Dependency Equation Generator 640. These dependency equations can also be used by the provenance model validator 650 to validate the compliance of provenance I-O dependency assertions made by application developers at the Integrated Development Environment 655.

Figure 3:
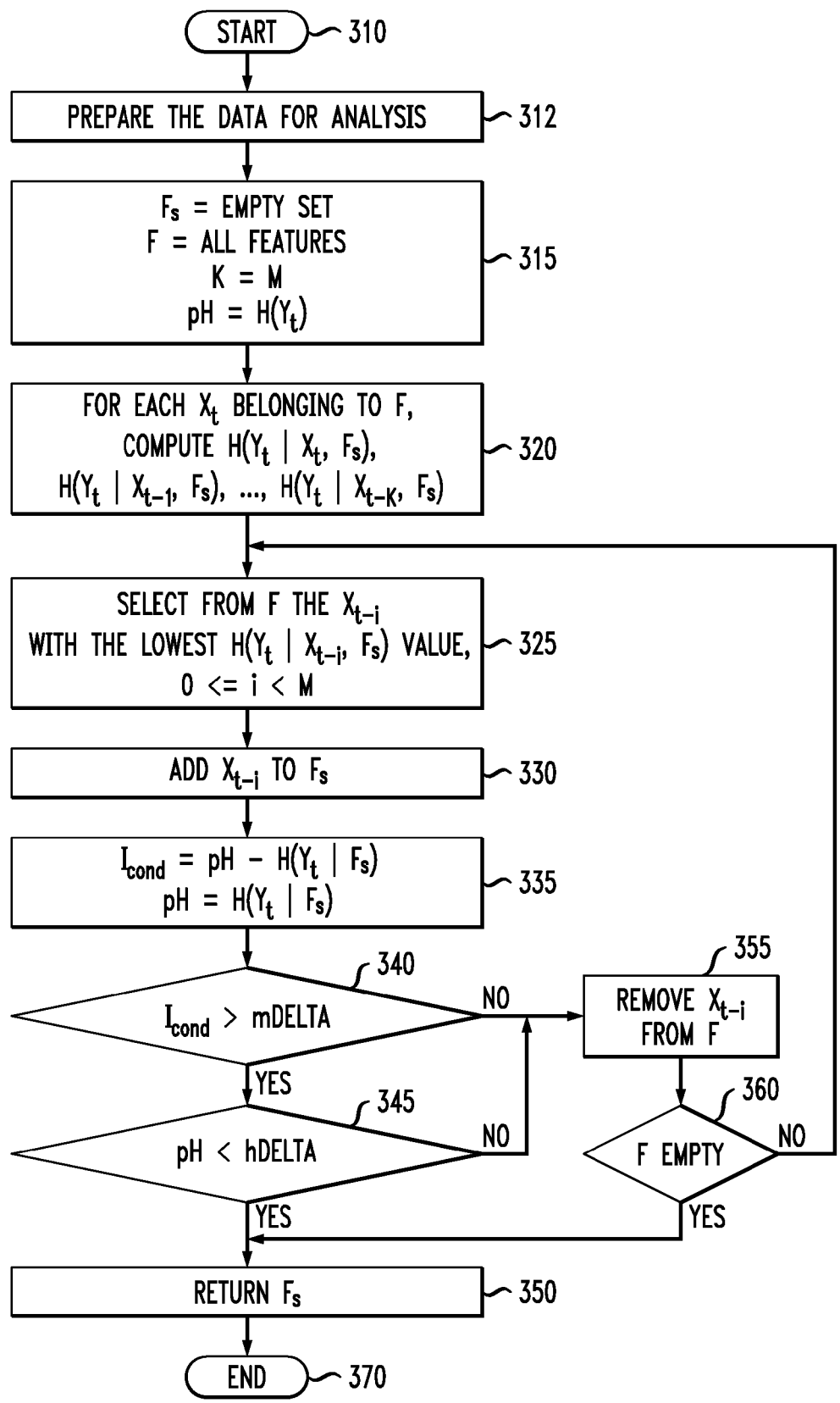
FIG. 3 illustrates a method for dominant component analysis, according to an embodiment of the invention.

FIG. 3 depicts a preferred embodiment for the method used to perform the dominant component analysis of module 635. This analysis starts (310) with a preparation of the data (312) in an empirical matrix, in the format shown in FIG. 2. Essentially, streams are vectorized, into vectors 215, 220, 225, 230, 235 of size M. To each of these vectors is attached an output element 240, 245, 250, 255, 250 corresponding to the output $Y_t$ generated for the corresponding input vector. Once the data is prepared, a set of variables are initialized (315) for the dominant component analysis. The set F of features of interest is set. Its cardinality (initially M) is stored in the variable K. An empty set $F_s$ of dominant features is initialized. Finally, the Shannon entropy [see C. E. Shannon, "A mathematical theory of communication," Bell System Technical Journal, vol. 27, pp. 379-423 and 623-656, July and October, 1948, the disclosure of which is incorporated herein] of the output process $Y_t$ is computed and assigned to the variable pH. In the next step (320), for each feature $X_{t-i}$ belonging to F, the conditional entropy $H(Y_t|X_{t-i})$ is computed. In step 325, the $X_{t-i}$ with the lowest conditional entropy $H(Y_t|X_{t-i}, F_s)$, is selected from F and added (330) to $F_s$. In the next step (335), a conditional mutual information $I_{cond}$ is computed by taking the difference between pH and $H(Y_t|F_S)$.

If $I_{cond}$ is greater (340) than a predefined threshold mDelta, then we conclude that the current feature set $F_S$ contributes to the prediction of $Y_t$. To further test if the dependency of $Y_t$ on $F_S$ is high enough, we test (345) the value of $H(Y_t|F_S)$. If this value is (345) below a threshold hDelta, we return $F_S$ (350) as the output of the analysis and end the computation (370). If this value is above hDelta, we remove $X_{t-i}$ from F and resume the computation at step 325, if F is not empty (360). If $I_{cond}$ is smaller (340) than mDelta, $X_{t-i}$ is removed from F (355) and the computation resumed at step 360.

Figure 4:
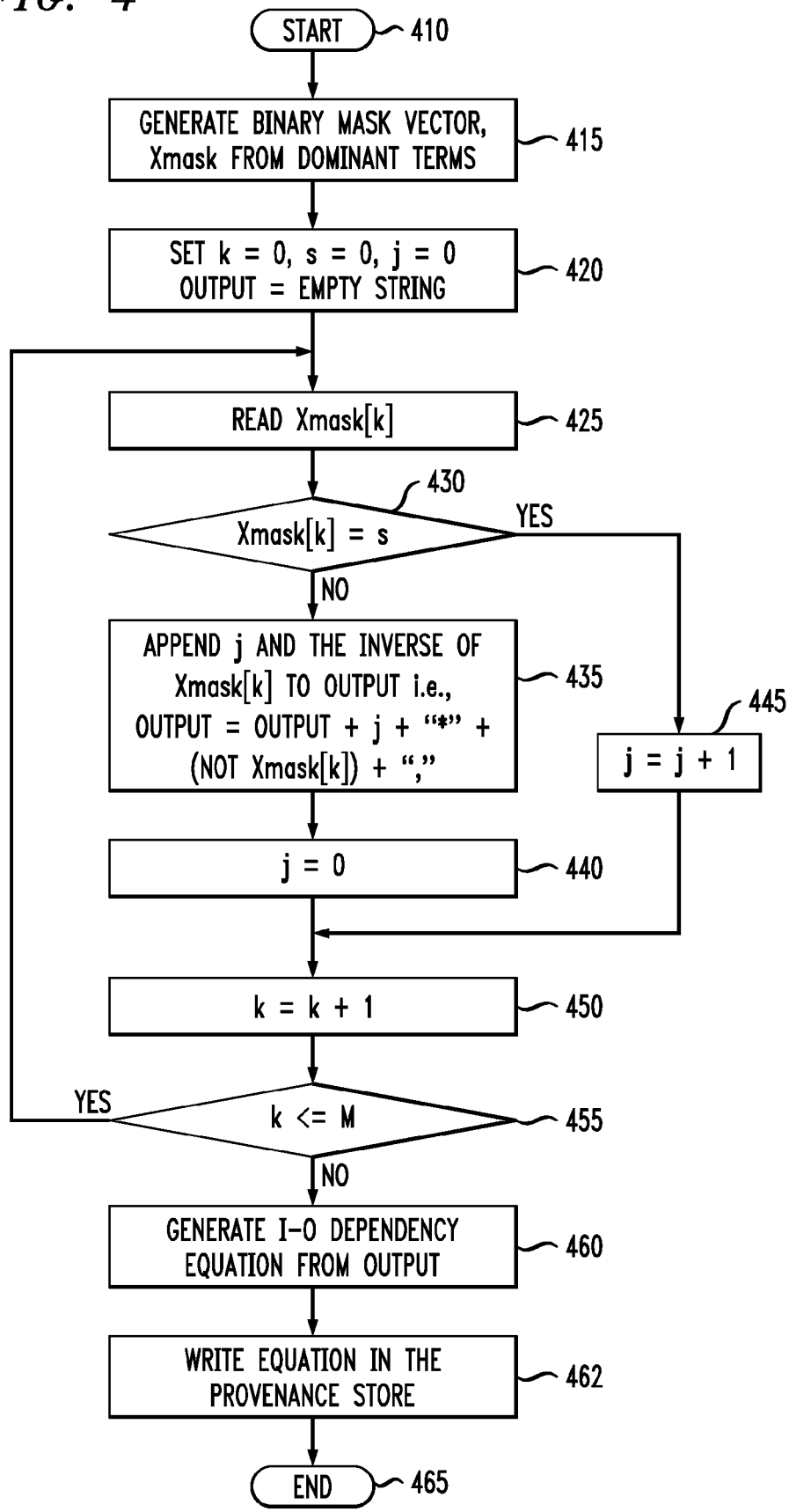
FIG. 4 illustrates a method for input-output dependency equation generation, according to an embodiment of the invention.

FIG. 4 shows a flow chart of a preferred embodiment for the computation taking place inside the I-O Dependency Equation Generator 640. In this embodiment, the computation starts (410) with a generation (415) of a binary mask vector Xmask from the dominant terms computed by the dominant component analysis module 635. Xmask is a binary vector of size M, with elements Xmask[i] equal to one if the term at position i in X is dominant. Conversely, Xmask[i] is equal to zero if the term at position i in X is not dominant. The next step (420) initializes variables needed for the rest of the computation. These variables are counters "k" and "j" which are set to 0, a binary state variable "s" which is set to 0, and a string "output" which is initially empty. The counter k tracks the number of features processed by this module. Consequently, its maximal value is M. j is used to track run lengths of 0 and 1 in Xmask.

The next step reads the value of Xmask[k] (425). We then test the value of Xmask[k] and compare it with s (430). If Xmask[k] is not equal to s, we append "j*(NOT Xmask[k])," to the output string (435), and set (440) j to 0, s to Xmask[k]. (NOT Xmask[k]) refers to the binary inversion of the Xmask [k] bit. The computation then executes step 450. If Xmask[k] is equal to s, j is incremented by 1 (445) and the computation then executes step 450. In step 450, k is incremented by 1. The next steps check if we have read all the elements of Xmask (455). This is done by checking if k is less or equal to M. If the answer is true, we have more elements to process and the computation loops back to step 425. If the answer is no, the next step is to use the output, which is a run length encoding of Xmask, and translate it into an I-O dependency equation (460), before storing it (462) in the provenance store. The computation ends in step 465.

Figure 5:
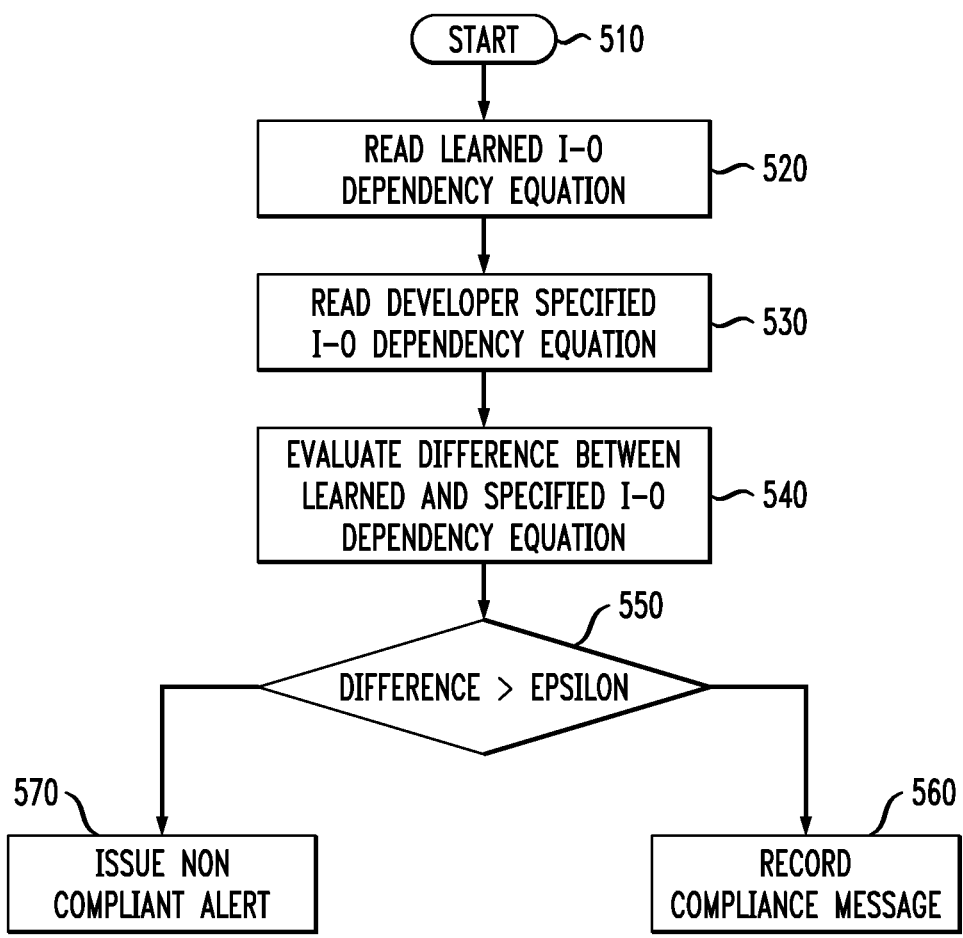
FIG. 5 illustrates a method for validating a provenance model, according to an embodiment of the invention.

FIG. 5 shows a technique proposed for the computation taking place inside the provenance model validator (650 in FIG. 6). The computation starts (510) by reading learned I-O dependency equations for a given processing element (520), followed by a read of developer specified I-O dependency equations. The next step evaluates differences between what the system has evaluated and what the developer has specified. If the difference is greater than epsilon (550), according to an arbitrary distance metric, a non-compliance alert is issued (570). This alert might be consumed by an administrator. Otherwise, if the distance is less or equal to epsilon, we record a compliance message (550).

Figure 7:
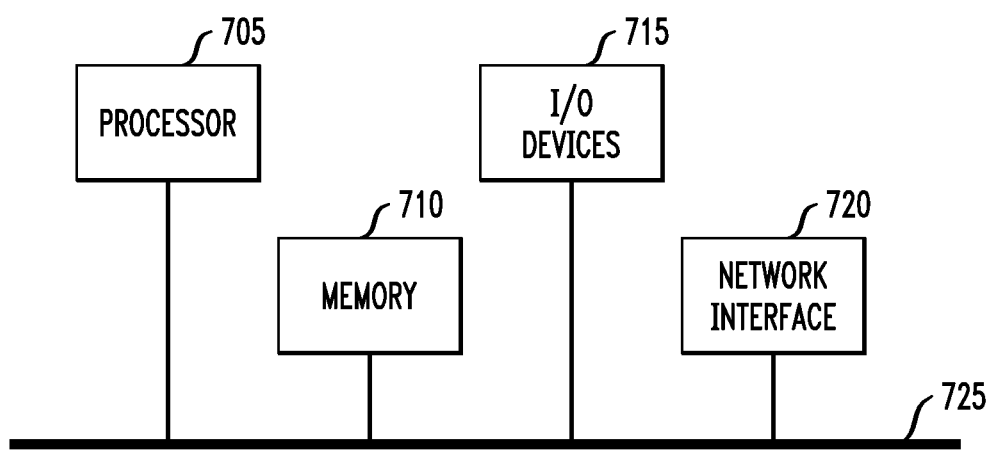
FIG. 7 illustrates a computer system in accordance with which one or more components/steps of the techniques of the invention may be implemented, according to an embodiment of the invention.

Lastly, FIG. 7 illustrates a computer system in accordance with which one or more components/steps of the techniques of the invention may be implemented. It is to be further understood that the individual components/steps may be implemented on one such computer system or on more than one such computer system. In the case of an implementation on a distributed computing system, the individual computer systems and/or devices may be connected via a suitable network, e.g., the Internet or World Wide Web. However, the system may be realized via private or local networks. In any case, the invention is not limited to any particular network.

Thus, the computer system shown in FIG. 7 may represent one or more servers or one or more other processing devices capable of providing all or portions of the functions described herein. Alternatively, FIG. 7 may represent a mainframe computer system.

The computer system may generally include a processor 705, memory 710, input/output (I/O) devices 715, and network interface 720, coupled via a computer bus 725 or alternate connection arrangement.

It is to be appreciated that the term "processor" as used herein is intended to include any processing device, such as, for example, one that includes a CPU and/or other processing circuitry. It is also to be understood that the term "processor" may refer to more than one processing device and that various elements associated with a processing device may be shared by other processing devices.

The term "memory" as used herein is intended to include memory associated with a processor or CPU, such as, for example, RAM, ROM, a fixed memory device (e.g., hard disk drive), a removable memory device (e.g., diskette), flash memory, etc. The memory may be considered a computer readable storage medium.

In addition, the phrase "input/output devices" or "I/O devices" as used herein is intended to include, for example, one or more input devices (e.g., keyboard, mouse, etc.) for entering data to the processing unit, and/or one or more output devices (e.g., display, etc.) for presenting results associated with the processing unit.

Still further, the phrase "network interface" as used herein is intended to include, for example, one or more transceivers to permit the computer system to communicate with another computer system via an appropriate communications protocol.

Accordingly, software components including instructions or code for performing the methodologies described herein may be stored in one or more of the associated memory devices (e.g., ROM, fixed or removable memory) and, when ready to be utilized, loaded in part or in whole (e.g., into RAM) and executed by a CPU.

In any case, it is to be appreciated that the techniques of the invention, described herein and shown in the appended figures, may be implemented in various forms of hardware, software, or combinations thereof, e.g., one or more operatively programmed general purpose digital computers with associated memory, implementation-specific integrated circuit(s), functional circuitry, etc. Given the techniques of the invention provided herein, one of ordinary skill in the art will be able to contemplate other implementations of the techniques of the invention.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

What is claimed is:

1. A method for processing data associated with a data stream received by a data stream processing system, wherein the system comprises a plurality of processing elements, the method comprising the steps of:
    obtaining a data stream of input elements and a data stream of output elements associated with at least one processing element of the plurality of processing elements, wherein the data stream of input elements are obtained from at least one streaming data source, and wherein the data stream of output elements are generated by the at least one processing element in response to the data stream of input elements;
    computing one or more intervals for the at least one processing element, wherein the one or more intervals are computed using data representing observations of associations between the input elements and the output elements of the at least one processing element, wherein, for a given one of the computed intervals, one or more particular input elements contained within the given computed interval are determined to have contributed to a particular output element; and
    using the computed one or more intervals to determine a dependency function that enables a provenance of the particular output element to be determined in terms of the one or more particular input elements.

2. The method of claim 1, wherein the one or more intervals are inferred offline using previously observed and stored sets of input elements and corresponding output elements.

3. The method of claim 1, wherein the one or more intervals are inferred online by using sets of newly observed input elements and corresponding output elements to continually increase the observed data being used, and continually refining the computation of the intervals to utilize the additional observed data.

4. The method of claim 1, wherein the one or more intervals are inferred using a combination of offline and online techniques.

5. The method of claim 1, wherein the observed data comprises actual input and output elements generated by external processes or events, as part of a normal operation of the data stream processing system.

6. The method of claim 1, wherein the observed data comprises input elements that are generated for one or more probe purposes as part of the interval computing step, and their corresponding output elements.

7. The method of claim 1, wherein the one or more intervals are computed using one or more statistical analysis methods over sets of input elements and their corresponding output elements generated by the data stream processing system.

8. The method of claim 7, wherein one of the statistical analysis methods uses entropy-based computations on empirical joint distributions of the input and output elements.

9. The method of claim 1, wherein the one or more intervals are computed using one or more linear transformations over sets of input elements and their corresponding output elements generated by the data stream processing system.

10. The method of claim 1, wherein the interval computing step further comprises using a specified confidence parameter that determines a length of the interval established.

11. The method of claim 10, wherein the confidence parameter is specified as part of a query.

12. The method of claim 1, wherein the one or more computed intervals comprise one or more time intervals computed on the input elements that affect the generation of the corresponding output elements.

13. The method of claim 1, wherein the one or more computed intervals comprise one or more sequence intervals computed on the input elements that affect the generation of the corresponding output elements.

14. The method of claim 1, wherein the step of using observations of associations between input and output elements further comprises using all of the input and output elements that have been observed within a specified past history.

15. The method of claim 1, wherein the step of using observations of associations between input and output elements further comprises using, for each output element, only a subset of the corresponding input elements, wherein the subset is obtained via filtering the total set of input elements using an externally specified filtering criterion.

16. A method for processing data associated with a data stream received by a data stream processing system, wherein the system comprises a plurality of processing elements, the method comprising the steps of:
    obtaining input data elements and output data elements associated with at least one processing element of the plurality of processing elements, wherein the input data elements are obtained from at least one streaming data source;
    specifying one or more intervals for the processing element wherein, for a given one of the intervals, one or more particular input elements contained within the given interval are believed to have contributed to a particular output element thereby determining a provenance of the particular output element in terms of the one or more particular input elements; and
    validating the one or more specified intervals by computing one or more intervals for the processing element using data representing observations of associations between inputs elements and output elements of the processing element, and comparing the one or more specified intervals and the one or more computed intervals.

17. The method of claim 16, further comprising the step of generating an alert notification when a difference between comparing the one or more specified intervals and the one or more computed intervals exceeds a specified threshold.

18. Apparatus for processing data associated with a data stream received by a data stream processing system, wherein the system comprises a plurality of processing elements, the apparatus comprising:
a memory; and
a processor coupled to the memory and configured to:
obtain a data stream of input elements and a data stream of output elements associated with at least one processing element of the plurality of processing elements, wherein the data stream of input elements are obtained from at least one streaming data source, and wherein the data stream of output elements are generated by the at least one processing element in response to the data stream of input elements;
compute one or more intervals for the at least one processing element, wherein the one or more intervals are computed using data representing observations of associations between the input elements and the output elements of the at least one processing element, wherein, for a given one of the computed intervals, one or more particular input elements contained within the given computed interval are determined to have contributed to a particular output element; and
use the computed one or more intervals to determine a dependency function that enables a provenance of the particular output element to be determined in terms of the one or more particular input elements.

19. The method of claim 18, wherein the one or more computed intervals comprise at least one of:

one or more time intervals computed on the input elements that affect the generation of the corresponding output elements; and
one or more sequence intervals computed on the input elements that affect the generation of the corresponding output elements.

20. An article of manufacture for processing data associated with a data stream received by a data stream processing system, wherein the system comprises a plurality of processing elements, the article comprising a computer readable storage medium having one or more programs embodied therewith wherein the one or more programs, when executed by a computer, perform steps of:
obtaining a data stream of input elements and a data stream of output elements associated with at least one processing element of the plurality of processing elements, wherein the data stream of input elements are obtained from at least one streaming data source, and wherein the data stream of output elements are generated by the at least one processing element in response to the data stream of input elements;
computing one or more intervals for the at least one processing element, wherein the one or more intervals are computed using data representing observations of associations between the input elements and the output elements of the at least one processing element, wherein, for a given one of the computed intervals, one or more particular input elements contained within the given computed interval are determined to have contributed to a particular output element; and
using the computed one or more intervals to determine a dependency function that enables a provenance of the particular output element to be determined in terms of the one or more particular input elements.

\* \* \* \* \*